US011319367B2

(12) United States Patent
Cook et al.

(10) Patent No.: US 11,319,367 B2
(45) Date of Patent: May 3, 2022

(54) COMPOSITIONS AND METHODS OF USE OF INTERLEUKIN-10 PEPTIDES AND ANTI-INTERLEUKIN-10 ANTIBODIES

(71) Applicant: WISCONSIN ALUMNI RESEARCH FOUNDATION, Madison, WI (US)

(72) Inventors: Mark Eric Cook, Madison, WI (US); Jordan Marshall Sand, Madison, WI (US); Sheila Mary McGuirk, Madison, WI (US); Jane Ellen Rieman, Davis, IL (US); Sarah Marie Raabis, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 133 days.

(21) Appl. No.: 16/596,839

(22) Filed: Oct. 9, 2019

(65) Prior Publication Data
US 2020/0031921 A1    Jan. 30, 2020

Related U.S. Application Data

(63) Continuation of application No. 14/670,636, filed on Mar. 27, 2015, now abandoned.

(51) Int. Cl.
| | |
|---|---|
| C07K 16/24 | (2006.01) |
| A23C 9/152 | (2006.01) |
| A61K 39/00 | (2006.01) |
| A61K 38/08 | (2019.01) |
| A23L 33/00 | (2016.01) |
| A23L 33/18 | (2016.01) |
| A61P 33/00 | (2006.01) |

(52) U.S. Cl.
CPC .......... *C07K 16/244* (2013.01); *A23C 9/1526* (2013.01); *A23L 33/18* (2016.08); *A23L 33/40* (2016.08); *A61K 38/08* (2013.01); *A61P 33/00* (2018.01); *A23V 2002/00* (2013.01); *A61K 2039/505* (2013.01); *A61K 2039/542* (2013.01); *C07K 2317/10* (2013.01); *C07K 2317/11* (2013.01); *C07K 2317/23* (2013.01); *C07K 2317/34* (2013.01)

(58) Field of Classification Search
CPC ....... A23L 33/18; A61P 11/00; A61K 38/2066
See application file for complete search history.

(56) References Cited

U.S. PATENT DOCUMENTS

| | | | | |
|---|---|---|---|---|
| 5,102,872 | A * | 4/1992 | Singh | A61K 38/2013 424/499 |
| 5,741,489 | A | 4/1998 | Pimentel | |
| 5,989,867 | A | 11/1999 | Knappe et al. | |
| 6,608,172 | B1 | 8/2003 | Chiou | |
| 8,652,457 | B2 * | 2/2014 | Sand | C07K 14/5428 424/85.2 |
| 9,505,836 | B2 | 11/2016 | Sand et al. | |
| 2006/0228448 | A1 | 10/2006 | Boileau et al. | |
| 2009/0022691 | A1 | 1/2009 | Moore et al. | |
| 2009/0186038 | A1 | 7/2009 | Reed | |
| 2013/0109619 | A1 | 5/2013 | Tarasova et al. | |
| 2014/0017248 | A1 | 1/2014 | Sand et al. | |
| 2014/0127220 | A1 | 5/2014 | Sand et al. | |
| 2015/0037277 | A1 | 2/2015 | Cook et al. | |
| 2016/0008436 | A1 | 1/2016 | Cook et al. | |
| 2019/0077859 | A1 | 3/2019 | Arendt et al. | |

FOREIGN PATENT DOCUMENTS

| | | |
|---|---|---|
| WO | 199404174 A1 | 3/1994 |
| WO | 199506657 A1 | 3/1995 |
| WO | 2008086621 A1 | 7/2008 |
| WO | 2015017132 A1 | 2/2015 |
| WO | 2016172722 A1 | 10/2016 |

OTHER PUBLICATIONS

Bowie et al. Science, 1990, 247:1306-1310 (Year: 1990).*
Burgess et al. J. Cell Biol. 111:2129-2138, 1990 (Year: 1990).*
Bork. Genome Research, 2000, 10:398-400 (Year: 2000).*
Lazar et al. Mol. Cell. Biol., 8:1247-1252, 1988 (Year: 1988).*
Paul. Fundamental Immunology, 3rd Edition, Raven Press, New York, Chapters, pp. 292-295, 1993 (Year: 1993).*
MacCallum et al. Antibody-antigen Interactions: Contact Analysis and Binding Site Topography. Journal of Molecular Biology, 262:732-745, 1996 (Year: 1996).*
Vajdos et al. Comprehensive Functional Maps of the Antigenbinding Site of an Anti-ErbB2 Antibody Obtained with Shotgun Scanning Mutagenesis. Journal of Molecular Biology, Jul. 5, 2002;320(2):415-28 (Year: 2002).*
Ferrara et al. Recombinant renewable polyclonal antibodies. mABs, 2015; 7(1): 32-41 (Year: 2015).*
Greenspan et al. Defining epitopes: It's not as easy as it seems. Nature Biotechnology 7: 936-937, 1999 (Year: 1999).*
"Anthelmintic Resistance: An Examination of its Growing Prevalence in the U.S. Cattle Herd", Executive Summary of the 2005 Anthelmintic Resistance Roundtable; http://www.merck-animal-health-usa.com/binaries/Anthel_Resist_Exec_Summary_2_tcm96-86774.pdf; 8 pages, (2005).
Alam et al.; "A2A Adenosine Receptor (AR) Activation Inhibits Pro-inflammatory Cytokine Production by Human CD4+ Helper T Cells and Regulates Helicobacter-Induced Gastritis and Bacterial Persistence"; Mucosal Immunology; 2(3); pp. 232-242; (2009).
Alba-Hurtado et al.; "Immune Responses Associated with Resistance to Haemonchosis in Sheep"; BioMed Research International; 2013, Article ID 162158; 11 pages; (2013).

(Continued)

*Primary Examiner* — Nanessa L. Ford
*Assistant Examiner* — Sandra Dillahunt
(74) *Attorney, Agent, or Firm* — Cantor Colburn LLP

(57) ABSTRACT

Disclosed herein are methods of reducing a symptom of respiratory disease in a pre-weaned milk-fed mammal by orally administering an isolated antibody that specifically binds the interleukin-10 peptide or an anti-interleukin-10 antibody. Also included are methods of reducing mixing stress in human and non-human mammals by administering an isolated antibody that specifically binds the interleukin-10 peptide or an anti-interleukin-10 antibody. Further included are milk and food compositions including the interleukin-10 peptide or anti-interleukin-10 antibody.

4 Claims, 1 Drawing Sheet

Specification includes a Sequence Listing.

(56) References Cited

OTHER PUBLICATIONS

Aly et al.; "Agreement Between Bovine Respiratory Disease Scoring Systems for Pre-weaned Dairy Calves"; Animal Health Research Reviews; 15(2); pp. 148-150; (2014).
Arai et al.; "Effects of In Vivo Adminsitration of Anti-IL-10 Monoclonal Antibody on the Host Defence Mechanism Against Murine Salmonella Infection"; Immunology; pp. 381-388; (1995).
Bai et al.; "IL-10 Signaling Blockage Controls Murine West Nile Virus infection"; PLoS Pathog; 5(10); 13 pages; e1000610.doi:10.1371/journal.ppat.1000610; (2009).
Barnes et al.; "Selection of Different Genotype Larvae and Adult Worms for Anthelmintic Resistance by Persistent and Short-Acting Avermectin/Milbemycins"; International Journal for Parasitology; 31; pp. 720-727; (2001).
Bobeck et al.; "Oral Antibodies to Human Intestinal Alkaline Phosphatase Reduce Dietary Phytate Phosphate Bioavailability in the Presence of Dietary 1Alpha-hydroxycholecalciferol"; Poultry Science; 95; pp. 570-580; (2016)
Bobeck et al.; "Oral Peptide Specific Egg Antibody to Intestinal Sodium-dependent Phosphate Co-transporter-2b is Effective at Altering Phosphate Transport in Vitro and in Vivo"; Poultry Science: 94; pp. 1128-1137; (2015).
Bork, Peer; "Powers and Pitfalls in Sequence Analysis: The 70% Hurdle"; Genome Research; 10; pp. 398-400; (2000)
Bowie et al.; "Deciphering the Message in Protein Sequences: Tolerance to Amino Acid Substitutions"; Science; 247(4948); pp. 1306-1310; (1990).
Brown et al.; Tolerance to Single, but Not Multiple, Amino Acid Replacements in Antibody Vh CFR2: J. Immunol.; 156; pp. 3285-3291; (1996).
Burgess, et al.; "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue"; J.Cell. Biol. 111; pp. 2129-2138; (1990).
Campbell et al.; "Susceptability to Cryptosporidium Parvum Infections in Cytokine—and Chemokine-Receptor Knockout Mice"; Journal of Parasitology; 88(5); pp. 1014-1016; (2002).
Canals, et al.; "Cytokine Profile Induced by a Primary Infection with Ostertagia Ostertagi in Cattle"; Veterinary Immunology and Immunopathology; 58; pp. 63-75; (1997).
Chen et al.; "Oral Administration of a Combination of Select Lactic Acid Bacteria Strains to Reduce the Salmonella Invasion and Inflammation of Broiler Chicks"; Poultry Science; 91(9); pp. 2139-2147; (2012).
Coles et al.; "The Detection of Anthelmintic Resistance in Nematodes of Veterinary Importance"; Veterinary Parasitology; 136; pp. 167-185; (2006).
Collier et al.; "Coccidia-induced Mucogenesis Promotes the Onset of Necrotic Enteritis by Supporting Clostridium Perfringens Growth"; Veterinary Immunology and Immunopathology; 112; pp. 104-115; (2008).
Cook, M. E.; "Triennial Growth Symposium: A Review of Science Leading to Host-Targeted Antibody Strategies for Preventing Growth Depression Due to Microbial Colonization"; J. Animal Sci; 89; pp. 1981-1990; (2011).
Cruse et al.; Illustrated Dict. of Immunology, 2nd ed., CRC Press, p. 46; (2003).
De Meulenaer et al.; "Isolation and Purification of Chicken Egg Yolk Immunoglobulins: A Review"; Food and Agricultural Immunology; 13(4); pp. 275-288; (2001).
Den HARTOG et al.; "Modulation of Human Immune Responses by Bovine interleukin-10"; PLoS ONE; 6(3); pp. 1-10 (2011).
Erova et al.; Protective Immunity Elicited by Oral Immunization of Mice with Salmonella enterica Serovar Typhimurium Braun Lipoprotein (Lpp) and Acetyltransferase (MsbB); Frontiers Cell Infect and Microbiol; vol. 6; Article 148; 14 pages; (2016).
Fawzi et al.; "Intranasal Immunization of Lambs with Serine/Threonine Phosphatase 2A Against Gastrointestinal Nematodes"; Clinical and Vaccine Immunology; 20:9; pp. 1352-1359; (2013).
Ferrara et al.; "Recombinant Renewale Polyclonal Antibodies"; mAbs; 7(1); pp. 32-41; (2015).
Filho et al.; "Humoral and Cellular Immune Response Generated by Different Vaccine Programs Before and After Salmonella enteritidis Challenge in Chickens"; Vaccine; 30; pp. 7637-7643; (2012).
Ghebremicael et al.; "Association of Interleukin-10 Cluster Genes and Salmonella Response in the Chicken" Poultry Science; 87(1); pp. 22-26; (2008).
Greenspan et al.; "Defining Epitopes: It's Not as Easy as it Seems"; Nature Biotechnology; 7; pp. 936-937; (1999).
Hodek et al.; "Chicken Antibodies—Superior Alternative for Conventional Immunoglobulins": Proc. Indian Sci Acad; B69(4); pp. 461-468; (2003).
International Search Report and Written Opinion; International Application No. PCT/US2014/047002; International Filing Date Jul. 17, 2014; dated Dec. 12, 2014; 14 pages.
International Search Report and Written Opinion; International Application No. PCT/US2016/020590; International Filing Date Mar. 3, 2016; dated Aug. 9, 2016; 18 pages.
Lazar et al.; "Transforming Growth Factor α: Mutation of Aspartic Acid 47 and Leucine 48 Results in Different Biological Activities"; Molecular and Cellular Biology; pp. 1247-1252; (1988).
Lee et al.; "IL-10 Suppresses Bactericidal Response of Macrophages Against Salmonella typhimurium"; Journal of Microbiology; 49(6): pp. 1050-1053; (2011).
Li, Robert W. et al.; "Localized Complement Activation in the Development of Protective Immunity Against Ostertagia Ostertagi Infections in Cattle"; Veterinary Parasitology; 174; pp. 247-256; (2010).
Li, Robert W., et al.; "Local Inflammation as a Possible Mechanism of Resistance to Gastrointestinal Nematodes in Angus Heifers"; Veterinary Parasitology; 145; pp. 100-107p (2007).
MacCallum et al.; "Antibody-antigen Interactions: Contact Analysis and Binding Site Topography"; J. Mol. Biol. 262; pp. 732-745; (1996).
Nuflor; "Bovine Respiratory Diseases: A New Look at Causes and Signs of Disease"; found in MERCK Animal Health ; http://www.nuflor.com/diseases/brd-nlac.asp; 4 pages; printed Mar. 3, 2017.
Paul, Fundamental Immunology, Third Edition (textbook), "Fv Structure and Diversity in Three Dimensions" pp. 292-295; Raven Press, New York (1993).
Pereira, et al.; "Requirement of Dual Stimulation by Homologous Recombinant IL-2 and Recombinant IL-12 for the invitro Production of Interferon Gamma by Canine Peripheral Blood Mononuclear Cells"; BMC Research Notes; pp. 460-469:2014.
Reineke, et al.; "Mapping of the Interleukin-10/Interleukin-10 Receptor Combining Site"; Protein Science; vol. 7, pp. 951-960; Cambridge University Press; 1998; 10 pages.
Rothwell et al.; "Cloning and Characterization of Chicken IL-10 and Its Role in the Immune Response to Elmeria Maxima"; Journal of Immunology; 173; pp. 2675-2682; (2004).
Salazar et al.; "Systemic Salmonella Infection Requires Interleukin 10 Production in Mice"; Front. Immunol. Conference Abstract:IMMUNOCOLOMBIA2015 at the 11th Congress of the Latin American Association of Immunology, 2015; doi: 10.3389/conf.fimmu.2015.05.00144.
Sand et al. "Oral Antibody to Interleukin-10 Prevents Growth Suppression by Coccidia Infection"; from Poultry Science Association 101st Annual Meeting Abstracts; Abstract P310; Jul. 9-12, 2012; Poult.Sci. 91(suppl.1) p. 107.
Setta et al.; "Early Immune Dynamics Following Infection With Salmonella enterica Serovars Enteridis, Infantis, Pullorum and Gallinarum: Cytokine and Chemokine Gene Expression Profile and Cellular Changes of Chicken Cecal Tonsils"; Comparative Immunology pp. 397-410; (2012).
Symonds et al.; "Bifidobacterium Infantis 35624 Protects Against Salmonella-Induced Reductions in Digestive Enzyme Activity in Mice by Attenuation of the Host Inflammatory Response"; Clinical and Translational Gastroenterology; 3, e15; 10 pages; (2012) doi:10.1038/ctg.2.
U.S. Appl. No. 13/957,601, filed Aug. 2, 2013; NonFinal Office Action dated May 7, 2015; 21 pages.

(56) References Cited

OTHER PUBLICATIONS

U.S. Appl. No. 13/957,601, filed Aug. 2, 2013; co-pending application, Methods of Reducing *Salmonella* in Poultry.
Vajdos, et al.; Comprehensive Functional Maps of the Antigen-binding Site of an Anti-ErbB2 Antibody Obtained with Shotgun Scanning Mutagenesis; J. Mol. Biol. 320; pp. 415-428; (2002).
Wei et al.; "*Salmonella enterica* Serovar Typhi Piasmid Impairs Dendritic Cell Responses to Infection"; Curr Microbiol 65; pp. 133-140; (2012).
Williams, R.B.; "Anticcoccidial Vaccines for Broiler Chickens: Pathways to Success"; Avian Pathology; 31(4); pp. 317-353; (2002).
Yazwinski et al.; "Fecal Egg Count Reduction and Control Trial Determinations of Anthelmintic Efficacies for Several Parasiticides Utilizing a Single Set of Naturally Infected Calves"; Veterinary Parasitology; 164; pp. 232-241; (2009).

\* cited by examiner

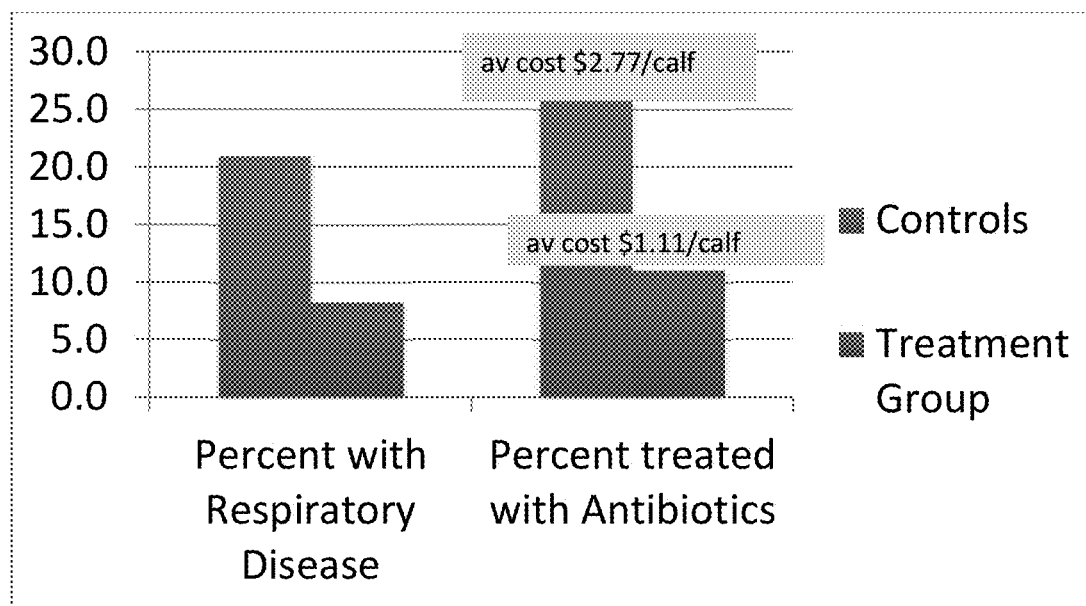

SEQUENCE LISTING

```
<160> NUMBER OF SEQ ID NOS: 38

<210> SEQ ID NO 1
<211> LENGTH: 7
<212> TYPE: PRT
<213> ORGANISM: Bos taurus

<400> SEQUENCE: 1

Asp Gln Leu His Ser Leu Leu
1               5

<210> SEQ ID NO 2
<211> LENGTH: 8
<212> TYPE: PRT
<213> ORGANISM: Bos taurus

<400> SEQUENCE: 2

Val Met Pro Gln Ala Glu Asn His
1               5

<210> SEQ ID NO 3
<211> LENGTH: 8
<212> TYPE: PRT
<213> ORGANISM: Bos taurus

<400> SEQUENCE: 3

Asp Ser Ser Cys Ile His Leu Pro
1               5

<210> SEQ ID NO 4
<211> LENGTH: 8
<212> TYPE: PRT
<213> ORGANISM: Bos taurus

<400> SEQUENCE: 4

Ser Glu Leu Gln Glu Arg Gly Val
1               5

<210> SEQ ID NO 5
<211> LENGTH: 7
<212> TYPE: PRT
<213> ORGANISM: Sus scrofa

<400> SEQUENCE: 5

Asp Gln Met Gly Asp Leu Leu
1               5

<210> SEQ ID NO 6
<211> LENGTH: 8
<212> TYPE: PRT
<213> ORGANISM: Sus scrofa

<400> SEQUENCE: 6

Val Met Pro Lys Ala Glu Ser Asp
1               5
```

```
<210> SEQ ID NO 7
<211> LENGTH: 8
<212> TYPE: PRT
<213> ORGANISM: Sus scrofa

<400> SEQUENCE: 7

Ser Lys Leu Gln Glu Arg Gly Val
1               5

<210> SEQ ID NO 8
<211> LENGTH: 8
<212> TYPE: PRT
<213> ORGANISM: Sus scrofa

<400> SEQUENCE: 8

Glu Asn Ser Cys Ile His Phe Pro
1               5

<210> SEQ ID NO 9
<211> LENGTH: 7
<212> TYPE: PRT
<213> ORGANISM: Ovis aries

<400> SEQUENCE: 9

Asp Gln Leu Asn Ser Met Leu
1               5

<210> SEQ ID NO 10
<211> LENGTH: 8
<212> TYPE: PRT
<213> ORGANISM: Ovis aries

<400> SEQUENCE: 10

Asn Met Leu Gln Glu Arg Gly Val
1               5

<210> SEQ ID NO 11
<211> LENGTH: 8
<212> TYPE: PRT
<213> ORGANISM: Ovis aries

<400> SEQUENCE: 11

Asp Ser Ser Cys Thr His Phe Pro
1               5

<210> SEQ ID NO 12
<211> LENGTH: 7
<212> TYPE: PRT
<213> ORGANISM: Bubalis bubalus

<400> SEQUENCE: 12

Asp Gln Leu Asp Ser Leu Leu
1               5

<210> SEQ ID NO 13
<211> LENGTH: 8
<212> TYPE: PRT
<213> ORGANISM: Bubalis bubalus

<400> SEQUENCE: 13

Ser Lys Leu Gln Asp Arg Gly Val
1               5

<210> SEQ ID NO 14
```

<211> LENGTH: 8
<212> TYPE: PRT
<213> ORGANISM: Bubalis bubalus

<400> SEQUENCE: 14

Asp Ser Ser Cys Thr Gln Phe Pro
1               5

<210> SEQ ID NO 15
<211> LENGTH: 8
<212> TYPE: PRT
<213> ORGANISM: Equus caballus

<400> SEQUENCE: 15

Asp Gln Leu Asp Asn Met Leu Leu
1               5

<210> SEQ ID NO 16
<211> LENGTH: 8
<212> TYPE: PRT
<213> ORGANISM: Equus caballus

<400> SEQUENCE: 16

Val Met Pro Gln Ala Glu Asn His
1               5

<210> SEQ ID NO 17
<211> LENGTH: 8
<212> TYPE: PRT
<213> ORGANISM: Equus caballus

<400> SEQUENCE: 17

Ser Lys Leu Gln Glu Lys Gly Val
1               5

<210> SEQ ID NO 18
<211> LENGTH: 8
<212> TYPE: PRT
<213> ORGANISM: Equus caballus

<400> SEQUENCE: 18

Glu Asn Ser Cys Thr His Phe Pro
1               5

<210> SEQ ID NO 19
<211> LENGTH: 8
<212> TYPE: PRT
<213> ORGANISM: Canis familiaris

<400> SEQUENCE: 19

Asp Lys Leu Asp Asn Ile Leu Leu
1               5

<210> SEQ ID NO 20
<211> LENGTH: 7
<212> TYPE: PRT
<213> ORGANISM: Canis familiaris

<400> SEQUENCE: 20

Val Met Pro Arg Ala Glu Asn
1               5

<210> SEQ ID NO 21
<211> LENGTH: 8
<212> TYPE: PRT

```
<213> ORGANISM: Canis familiaris

<400> SEQUENCE: 21

Ser Lys Leu Gln Glu Lys Gly Val
1               5

<210> SEQ ID NO 22
<211> LENGTH: 8
<212> TYPE: PRT
<213> ORGANISM: Canis familiaris

<400> SEQUENCE: 22

Glu Asp Asp Cys Thr His Phe Pro
1               5

<210> SEQ ID NO 23
<211> LENGTH: 8
<212> TYPE: PRT
<213> ORGANISM: Felis catus

<400> SEQUENCE: 23

Asp Glu Leu His Ser Ile Leu Leu
1               5

<210> SEQ ID NO 24
<211> LENGTH: 8
<212> TYPE: PRT
<213> ORGANISM: Felis catus

<400> SEQUENCE: 24

Val Met Pro Gln Ala Glu Asn Glu
1               5

<210> SEQ ID NO 25
<211> LENGTH: 8
<212> TYPE: PRT
<213> ORGANISM: Felis catus

<400> SEQUENCE: 25

Ser Lys Leu Gln Glu Lys Gly Val
1               5

<210> SEQ ID NO 26
<211> LENGTH: 8
<212> TYPE: PRT
<213> ORGANISM: Felis catus

<400> SEQUENCE: 26

Glu Asp Asn Cys Thr His Phe Ser
1               5

<210> SEQ ID NO 27
<211> LENGTH: 8
<212> TYPE: PRT
<213> ORGANISM: Lepus curpaeums

<400> SEQUENCE: 27

Asp Gln Leu Asn Ser Met Leu Leu
1               5

<210> SEQ ID NO 28
<211> LENGTH: 8
<212> TYPE: PRT
<213> ORGANISM: Lepus curpaeums
```

```
<400> SEQUENCE: 28

Val Met Pro Gln Ala Glu Asn His
1               5

<210> SEQ ID NO 29
<211> LENGTH: 8
<212> TYPE: PRT
<213> ORGANISM: Lepus curpaeums

<400> SEQUENCE: 29

Ser Lys Leu Gln Glu Glu Gly Val
1               5

<210> SEQ ID NO 30
<211> LENGTH: 8
<212> TYPE: PRT
<213> ORGANISM: Lepus curpaeums

<400> SEQUENCE: 30

Glu Asn Ser Cys Ile His Phe Pro
1               5

<210> SEQ ID NO 31
<211> LENGTH: 8
<212> TYPE: PRT
<213> ORGANISM: Cavia porcellus

<400> SEQUENCE: 31

Asp Gln Leu Asp Asn Val Leu Leu
1               5

<210> SEQ ID NO 32
<211> LENGTH: 8
<212> TYPE: PRT
<213> ORGANISM: Cavia porcellus

<400> SEQUENCE: 32

Val Met Pro Gln Ala Glu Lys His
1               5

<210> SEQ ID NO 33
<211> LENGTH: 8
<212> TYPE: PRT
<213> ORGANISM: Cavia porcellus

<400> SEQUENCE: 33

Asn Lys Leu Gln Asp Gln Gly Val
1               5

<210> SEQ ID NO 34
<211> LENGTH: 8
<212> TYPE: PRT
<213> ORGANISM: Cavia porcellus

<400> SEQUENCE: 34

Glu Asp Ser Cys Ala His Phe Pro
1               5

<210> SEQ ID NO 35
<211> LENGTH: 7
<212> TYPE: PRT
<213> ORGANISM: Homo sapiens

<400> SEQUENCE: 35
```

```
Asp Gln Leu Asp Asn Leu Leu
1               5

<210> SEQ ID NO 36
<211> LENGTH: 8
<212> TYPE: PRT
<213> ORGANISM: Homo sapiens

<400> SEQUENCE: 36

Val Met Pro Gln Ala Glu Asn Gln
1               5

<210> SEQ ID NO 37
<211> LENGTH: 8
<212> TYPE: PRT
<213> ORGANISM: Homo sapiens

<400> SEQUENCE: 37

Asn Lys Leu Gln Glu Lys Gly Ile
1               5

<210> SEQ ID NO 38
<211> LENGTH: 8
<212> TYPE: PRT
<213> ORGANISM: Homo sapiens

<400> SEQUENCE: 38

Glu Asn Ser Cys Thr His Phe Pro
1               5
```

COMPOSITIONS AND METHODS OF USE OF INTERLEUKIN-10 PEPTIDES AND ANTI-INTERLEUKIN-10 ANTIBODIES

CROSS-REFERENCE TO RELATED APPLICATIONS

This application is a continuation of U.S. application Ser. No. 14/670,636 filed on Mar. 27, 2015, which is incorporated herein by reference in its entirety.

FIELD OF THE DISCLOSURE

The present disclosure is related to compositions containing interleukin-10 peptides and anti-interleukin-10 antibodies and to their methods of use in the treatment of humans and other mammals.

BACKGROUND

Interleukin-10 (IL-10) peptides and anti-IL-10 antibodies have been described in U.S. Pat. No. 8,652,457, as well as their use to treat gastrointestinal protozoan infections in animals. In particular, isolated anti-IL-10 antibodies were shown to prevent growth suppression due to Coccidiosis infection in chicks, and injection of IL-10 peptides into hens was shown to passively transfer anti-IL-10 antibodies to chicks to prevent growth suppression caused by Coccidia infection. Animal feeds and animal feed additives containing the IL-10 peptides and anti-IL-10 antibodies were described.

What is needed are additional methods for the treatment and/or prevention of additional diseases and conditions in animals.

BRIEF SUMMARY

In an aspect, a method of reducing a symptom of respiratory disease in a pre-weaned milk-fed mammal comprises orally administering to the pre-weaned milk-fed mammal an effective amount of an interleukin-10 peptide or an isolated antibody that specifically binds an interleukin-10 peptide, wherein administration is initiated between birth and weaning, and wherein administration is performed at least once daily for a period of 7 days to 7 weeks.

In another aspect, a method of reducing mixing stress in a mammal comprises orally administering to the mammal an effective amount of an interleukin-10 peptide or an isolated antibody that specifically binds an interleukin-10 peptide, wherein administration is initiated within four weeks of mixing the mammal with a new population of mammals, and wherein administration is performed at least once daily for a period of 7 days to 7 weeks.

In yet another aspect, a method of reducing mixing stress in a human child comprises orally administering to the human child an effective amount of an interleukin-10 peptide or an isolated antibody that specifically binds an interleukin-10 peptide, wherein administration is initiated within four weeks of mixing the human child with a new population of human children, and wherein administration is performed at least once daily for a period of 7 days to 7 weeks.

Also included herein is a milk composition suitable for administration to a pre-weaned mammal of a genus *Bos, Ovis, Capra, Bubalus*, or *Sus* that comprises a basal milk composition and a therapeutically effective amount of an interleukin-10 peptide or an isolated antibody that specifically binds the interleukin-10 peptide.

Further included herein is a food composition suitable for administration to a human that comprises a basal food composition and a peptide of SEQ ID NO. 35, SEQ ID NO. 36, SEQ ID NO. 37, or SEQ ID NO. 38; or an isolated anti-IL-10 antibody that specifically binds a peptide of SEQ ID NO. 35, SEQ ID NO. 36, SEQ ID NO. 37, or SEQ ID NO. 38.

BRIEF DESCRIPTION OF THE DRAWINGS

FIG. 1 shows reduced respiratory disease and antibiotic usage in pre-weaned calves fed an anti-IL-10 antibody in the field trial of Example 2.

The above-described and other features will be appreciated and understood by those skilled in the art from the following detailed description, drawings, and appended claims.

DETAILED DESCRIPTION

Described herein are methods of reducing the incidence of disease and stress in mammals by orally administering IL-10 peptides and/or anti-IL-10 antibodies. It has been unexpectedly shown herein that oral administration of an anti-IL-10 antibody increased hipometer measurement, reduced the incidence of bovine respiratory disease, and decreased antibiotic use in pre-weaned calves. Because the IL-10 peptides and anti-IL-10 antibodies can improve respiratory immunity as well as gastrointestinal immunity, the IL-10 peptides and anti-IL-10 antibodies can be used to reduce the symptoms of a variety of stresses in mammals, such as the stress associated with mixing populations of mammals.

Young pre-weaned mammals such as dairy calves are susceptible to dairy calf pneumonia, referred to as Bovine Respiratory Disease Complex. Bovine respiratory disease complex (BRD) is a significant cause of morbidity, mortality and animal welfare concern and costs the industry between $800-900 million annually. Antibiotic treatment is costly, recurrence rates are high, the development of refractory sequelae are common, and antibiotic resistance is a concern. Thus, there is a need for improved treatment of pre-weaned mammals that are susceptible to respiratory infections, including mammals of a genus *Bos* (calves/cows), *Ovis* (lambs/sheep), *Capra* (kids/dairy goats), *Sus* (piglets/pigs) and *Bubalus* (calf/water buffalo), particularly milk-fed mammals.

In one embodiment, a method of reducing a symptom of respiratory disease in a pre-weaned milk-fed mammal comprises orally administering to the pre-weaned milk-fed mammal an effective amount of an interleukin-10 peptide or an isolated antibody that specifically binds an interleukin-10 peptide, wherein administration is initiated between birth and weaning, such as within 1 to 3 days of birth, and wherein administration is performed at least once daily for a period of 7 days to 7 weeks, specifically 7 days to three, four, five or six weeks, more specifically 7 days to 2 weeks. In one embodiment, the treated mammal is a bovine that exhibits reduced evidence of respiratory disease at 56 days of age compared to a control untreated pre-weaned bovine (FIG. 1). In certain aspects, administration of the IL-10 peptide or anti-IL-10 antibody is stopped after the treatment period, e.g., a 7 day to 7 week treatment period. In another aspect, administration of the IL-10 peptide or anti IL-10 antibody is not restarted for at least 1 to 14 days, specifically 7 to 14 days. In a specific aspect, the pre-weaned milk-fed mammal is a Bovine (a calf), and the respiratory disease is bovine respiratory disease. In other aspects, the pre-weaned milk-fed mammal is a sheep, a dairy goat, or a water buffalo.

As used herein, the term weaning means the practice of separating a mammal such as a calf from its source of milk. Calves are generally separated from their mothers shortly after birth and are fed whole milk or a milk replacer until weaning from their milk source, generally at 28 to 56 days of age. Calves that are raised apart from their mothers can be referred as housed calves and are generally housed in individual pens or in small groups. Nursing calves, however, can also be supplemented with milk or milk replacer. Thus, a pre-weaned mammal is a baby mammal that receives the majority of its nutrition from milk. As used herein, milk-fed means that a mammal is fed either whole milk, waste milk or milk replacer as their primary source of nutrition. Milk replacer, in the case of calves, generally includes protein such as whey protein or casein, but can also contain soy protein for example. In addition, milk replacers include fat such as animal fat or vegetable oil, essential amino acids, vitamins and minerals.

In one aspect, a pre-weaned calf is a calf that is 56 days old or younger. In the case of goats and sheep, weaning is usually based on weight, however, weaning generally occurs at 6-8 weeks of age, or longer. Weaning of water buffalo is longer than cows, generally at 90 days or more.

Symptoms of respiratory disease include elevated rectal temperature, cough, nasal discharge, ocular discharge, and/or ear droop. Diarrhea can be caused by fecal pathogens including *Cryptosporidium parvum* and is frequently associated with a reduced appetite, abnormal attitude, dehydration, reduced weight gain, and/or decreased fecal pH. Respiratory disease and diarrhea are the two most important diseases of preweaned calves.

Fecal pH, specifically a neutral fecal pH, may be an indication of improved digestion and gastrointestinal health. In certain aspects, fecal pH can be used as an indication of the health of the gastrointestinal tract of a calf. A pH of 5.5 to 7.4 is indicative of a healthy calf, while a pH of less than 5.5 or greater than 7.4 may be indicative of digestive tract dysfunction.

In one aspect, the IL-10 peptide or anti-IL-10 antibody is administered in the form of a milk composition. As used herein, the term milk includes whole milk, waste milk, or a milk replacer composition.

It was unexpectedly found herein that oral administration of anti-IL-10 antibodies, which had previously been shown to reduce gastrointestinal parasites, can also be used to improve respiratory immunity. Administration of IL-10 peptides and/or IL-10 antibodies is expected to reduce the use of antibiotics in treated mammals, resulting in a significant cost savings. Broad spectrum antibiotics such as NUFLOR® (florfenicol), Excede® (ceftiofur), Draxxin® (tulathromycin), Baytril® 100 (enrofloxacin) and Zuprevo® (tildipirosin) are used to treat BRD associated with *Mannheimia (Pasteurella) haemolytica, Pasteurella multocida*, and *Histophilus somni*, for example. Because the immunity provided by the IL-10 peptides and/or IL-10 antibodies is expected to last past weaning, protection of post-weaned animals from BRD is expected.

Effective amount of the interleukin-10 peptide or the isolated antibody that specifically binds an interleukin-10 peptide for the treatment of mammals are 3 g/kg (dry matter) milk to 0.001 mg/Kg (dry matter) milk, specifically 1 g/Kg (dry matter) milk to 0.341 g/Kg (dry matter) milk.

In another embodiment, young and adult mammals are subject to stress related to introducing them to a new population of mammals, a process referred to herein as "mixing." The stress associated with mixing a mammal into a new population of mammals is referred to herein as "mixing stress." The term mammals includes both human and non-human mammals. In addition to the stress from exposing the mammal to a new population of mammals and any illness within that population, stress can be induced by moving a mammal from familiar surroundings and exposing the mammal to any combination of shipping crates, new foods, temperature changes, means of transportation, and new handlers or caregivers. Stress can result from transport, comingling, feeding changes, vaccination, animal management procedures, crowding, auction, temperature fluctuations, and the like. Stress can affect the immune system of these animals resulting in weight loss (referred to as shrink in cows), fatigue, lack of appetite, signs of depression, and even death. All mammals, including for example, animals of genus *Bos* (calves/cows), *Ovis* (lambs/sheep), *Capra* (kids/dairy goats), *Sus* (piglets/pigs) and *Bubalus* (calf/water buffalo), are subject to mixing stress. Additional animals that are subject to mixing stress include horses, dogs, cats, rabbits, and guinea pigs. Mixing stress can occur whether or not the new population is infected with a known illness, such as a viral or bacterial infection.

Thus, a method of reducing mixing stress in a mammal comprises orally administering to the mammal an effective amount of an interleukin-10 peptide or an isolated antibody that specifically binds an interleukin-10 peptide, wherein administration is initiated within four weeks of mixing the mammal with a new population of mammals, and wherein administration is performed at least once daily for a period of 7 days to 7 weeks, specifically 7 days to three, four, five or six weeks, more specifically 7 days to 2 weeks. As used herein, within four weeks of mixing means that administration of the IL-10 peptide or anti-IL-10 antibody is initiated from 4 weeks prior to mixing with the new population to 4 weeks after mixing with the new population. In one embodiment, administration of the IL-10 peptide or anti-IL-10 antibody is stopped after the treatment period and is not restarted until 1 to 14 days, specifically 7 to 14 days. The IL-10 peptide or anti-IL-10 antibody can be administered in a food composition, such as a milk composition or an animal feed composition.

In one embodiment, when the mammal is a non-human mammal, the method further comprising exposing the non-human mammal to a shipping crate, new food, temperature change, a means of transportation, vaccination, castration, tail docking, branding, dehorning, a new handler, a new caregiver, or a combination thereof.

In the case of young mammals, calves for example, mixing stress can result in respiratory disease, weight loss, and behavioral changes. Mixing stress in pigs has been shown to have long-term adverse effects on immune function. In companion animals, moving of animals between shelters or adoption of an animal is often associated with an increased incidence of infectious diseases. Thus, methods of decreasing mixing stress in mammals is applicable across all species of mammals that are subject to mixing of populations.

Effective amount of the interleukin-10 peptide or the isolated antibody that specifically binds an interleukin-10 peptide for the treatment of mammals are 3 g/kg (dry matter) feed/food to 0.001 mg/Kg (dry matter) feed/food, specifically 1 g/Kg (dry matter) feed/food to 0.341 g/Kg feed/food.

In a specific aspect, human children are exposed to stress when they are mixed with a new population of children, such as in a new school or home, a new child care facility, or a new classroom. The move itself may weaken the immune system of the child and the child may be exposed to illnesses in the new population that the child was not previously exposed to. Introduction of a child into a new population of children can result in a variety of illness, including gastrointestinal and respiratory illnesses. Cryptosporidiosis, for example, is a common cause of diarrhea in child care settings. Viral and bacterial respiratory illnesses are also prevalent in childcare situations and schools. Thus, methods to reduce illness associated with mixing stress in human children are also desirable.

In one embodiment, a method of reducing mixing stress in a human child comprises orally administering to the human child an effective amount of an interleukin-10 peptide or an isolated antibody that specifically binds an interleukin-10 peptide, wherein administration is initiated within four weeks of mixing the human child with a new population of human children, and wherein administration is performed at least once daily for a period of 7 days to 7 weeks, specifically 7 days to three, four, five or six weeks, more specifically 7 days to 2 weeks.

In certain aspects, administration of the Il-10 peptide or anti-IL-10 antibody is stopped after the treatment period. As used herein, groups of children include school groups, such as a new school classroom, or a population of children in a childcare setting. The group of children can be as small as, for example, four to six children, to much larger classroom situations.

Reduction of mixing stress may be accompanied by a reduction in gastrointestinal and/or respiratory illness in the child, particularly illnesses associated with mixing of populations of children. Symptoms of illness include, for example, runny nose, cough, fever, listlessness, vomiting, diarrhea, earaches, sore throat, wheezing, and the like, and combinations thereof. Oral administration of an IL-10 peptide or an anti-Il-10 antibody is expected to improve the gastrointestinal and respiratory immunity of the child, thus reducing the symptoms of illness when exposed to new groups of children.

The IL-10 peptides and anti-IL-10 antibodies can be administered in the form of a pharmaceutical composition, or in the form of a food or beverage composition. Effective amount of the interleukin-10 peptide or the isolated antibody that specifically binds an interleukin-10 peptide for the treatment of mammals are depend on the level of isolation. The range of effective doses are shown in table 2.

As used herein, the term "peptide" includes the peptide as well as pharmaceutically acceptable salts of the peptide. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids.

As used herein, the term "antibody", or "immunoglobulin", encompasses naturally occurring antibodies, such as polyclonal and monoclonal antibodies, as well as artificial or synthetic antibodies or genetically engineered forms of antibodies, including single chain (domain) antibodies (e.g., camelid antibodies, chimeric, and bifunctional antibodies, as well as fragments thereof.

The term "isolated antibody" as used herein, refers to an antibody that is at least partially purified from other naturally associated molecules, or substantially free of antibodies having different antigenic specificities. In some cases, particularly in the case of egg yolk antibodies, the antibody may comprise 50-70% or more of an isolated antibody preparation.

An IL-10 peptide of the present disclosure includes the amino acid sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, and combinations thereof (see Table 1).

TABLE 1

Sequence ID NO. and Corresponding Amino Acid Sequence.

| SEQ ID NO. | AMINO ACID SEQUENCE | Organism |
| --- | --- | --- |
| SEQ ID NO. 1 | DQLHSLL | cow |
| SEQ ID NO. 2 | VMPQAENH | Cow/sheep/goat/water buffalo |
| SEQ ID NO. 3 | DSSCIHLP | cow |
| SEQ ID NO. 4 | SELQERGV | cow |
| SEQ ID NO. 5 | DQMGDLL | pig |
| SEQ ID NO. 6 | VMPKAESD | pig |
| SEQ ID NO. 7 | SKLQERGV | pig |
| SEQ ID NO. 8 | ENSCIHFP | pig |
| SEQ ID NO. 9 | DQLNSML | sheep/goat |
| SEQ ID NO. 10 | NMLQERGV | sheep/goat |
| SEQ ID NO. 11 | DSSCTHFP | sheep/goat |
| SEQ ID NO. 12 | DQLDSLL | water buffalo |
| SEQ ID NO. 13 | SKLQDRGV | water buffalo |
| SEQ ID NO. 14 | DSSCTQFP | water buffalo |
| SEQ ID NO. 15 | DQLDNMLL | horse |
| SEQ ID NO. 16 | VMPQAENH | horse |
| SEQ ID NO. 17 | SKLQEKGV | horse |
| SEQ ID NO. 18 | ENSCTHFP | horse |
| SEQ ID NO. 19 | DKLDNILL | dog, Canis lupis familiaris |
| SEQ ID NO. 20 | VMPRAEN | dog |
| SEQ ID NO. 21 | SKLQEKGV | dog |
| SEQ ID NO. 22 | EDDCTHFP | dog |
| SEQ ID NO. 23 | DELHSILL | cat, Felis catus |
| SEQ ID NO. 24 | VMPQAENE | cat |
| SEQ ID NO. 25 | SKLQEKGV | cat |
| SEQ ID NO. 26 | EDNCTHFS | cat |

TABLE 1-continued

Sequence ID NO. and Corresponding Amino Acid Sequence.

| SEQ ID NO. | AMINO ACID SEQUENCE | Organism |
|---|---|---|
| SEQ ID NO. 27 | DQLNSMLL | rabbit |
| SEQ ID NO. 28 | VMPQAENH | rabbit |
| SEQ ID NO. 29 | SKLQEEGV | rabbit |
| SEQ ID NO. 30 | ENSCIHFP | rabbit |
| SEQ ID NO. 31 | DQLDNVLL | guinea pig |
| SEQ ID NO. 32 | VMPQAEKH | guinea pig |
| SEQ ID NO. 33 | NKLQDQGV | guinea pig |
| SEQ ID NO. 34 | EDSCAHFP | guinea pig |
| SEQ ID NO. 35 | DQLDNLL | human |
| SEQ ID NO. 36 | VMPQAENQ | human |
| SEQ ID NO. 37 | NKLQEKGI | human |
| SEQ ID NO. 38 | ENSCTHFP | human |

SEQ ID NOs. 1-14 are amino acid sequences corresponding to peptides of the IL-10 cytokine in pre-weaned animals according to the present disclosure. SEQ ID NOs. 1-38 correspond to exemplary mammals subject to mixing stress.

The present disclosure further includes antibodies that specifically bind to the IL-10 peptides (also referred to herein as "anti-IL-10 antibody"). The antibodies of the present disclosure specifically bind to IL-10 peptides including the amino acid sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, and combinations thereof.

The present disclosure is further directed to generating antibodies that specifically bind to the IL-10 peptides. In one embodiment, an antibody is generated by administering the IL-10 peptides described above to an animal. Suitable animals to administer the IL-10 peptides for generating the antibodies include, for example, poultry. Exemplary poultry include chickens, turkeys, ducks, quail, and pheasant. Specific poultry include turkeys and chickens. Additional animals include livestock animals such as cattle, pigs, sheep, and fish.

Exemplary methods for administering the IL-10 peptides to the animal include injection and oral administration. Injection and oral administration optionally include use of an adjuvant such as, for example, Freund's Complete adjuvant and Cholera toxin. Administration optionally further includes conjugation of the IL-10 peptide to a carrier protein such as, for example, bovine gamma globulin or keyhole limpet hemocyanin.

In one embodiment, antibodies to the IL-10 peptides are generated by an animal (referred to herein as the "producer animal"). When the animal is an avian animal, as known by those skilled in the art, the antibodies generated are passed to the egg, and may specifically be concentrated in the egg yolk of the avian producer animal. Alternatively, antibodies of the present disclosure may be isolated from the animal itself such as from serum.

In one embodiment, the antibody is an avian egg yolk antibody. Egg yolks derived from a laying hen are inexpensive, convenient and can be safer to handle as compared to the hyperimmunized mammalian sera. Also, egg yolk antibodies are able to stand up to the scrutiny under modern animal protection regulations. Immunoglobulin Y (IgY) is an avian immunoglobulin.

To produce avian egg yolk antibodies, the IL-10 peptides are injected into laying fowl, such as hens, preferably at various intervals, to induce an immune response. The hens may be injected intramuscularly or sub-cutaneously. The specific mode of injection is not essential. It is well known that the IgY antibodies produced by the hens in response to such an immune challenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying methods, and the resulting dried powder may be encapsulated or otherwise used in oral dosage forms.

Alternatively, a procedure of partial purification or fractionation may be carried out to remove the majority of the non-aqueous bio-molecules and granules and optionally the majority of other proteins in the egg yolk. Exemplary purification techniques include the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, pH is about 5-7. Desirably, the temperature in this step is within about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include, but are not limited to, NaCl, $Na_2SO_4$, $(NH_4)_2SO_4$, KCl, $CaCl_2$, and $MgSO_4$. Specific salts include $Na_2SO_4$ and $(NH_4)_2SO_4$. The salt concentration for precipitating antibodies depends on the type of the salt. In one embodiment, the salt is present in an amount of higher than 15% and lower than 35% by weight, specifically between 20% and 30% by weight of the salt, on the basis of the final volume of the yolk supernatant.

Alternatively, the antibodies may be purified or isolated using any conventional technique such as by immunoaffinity purification.

In one embodiment, egg yolk antibodies are prepared by the following method. Laying hens are inoculated with IL-10 peptide. Optionally, an adjuvant is administered in conjunction with the IL-10 peptide to enhance the immunization. An adjuvant useful for this purpose is a water-in-oil emulsion adjuvant such as complete Freund's adjuvant. The IL-10 peptide causes the hens to produce anti-IL-10 antibodies which are passively transferred into the egg yolk of eggs laid by the hens.

Egg yolks or whole eggs containing the anti-IL-10 antibody can be collected and homogenized to form an emulsion. The resulting emulsion can be dried to form a powder containing the anti-IL-10 antibody. This powder can then be formulated in a manner appropriate to the administration route and then administered to the desired animals using methods known in the art. The preparation is preferably administered orally, such as in an oral dosage form or in a supplement to the animal's diet.

The antibodies that specifically bind to IL-10 peptides may be isolated and purified from animal serum or egg using a suitable method known in the art. Such methods include affinity chromatography, as well as other suitable methods for antibody isolation and purification known in the art and described in U.S. Pat. No. 6,608,172 and De Meulenaer et al., "Isolation and Purification of Chicken Egg Yolk Immunoglobulins: A Review," Food and Agricultural Immunology, Vol. 13(4), 2001, hereby incorporated by reference to the extent that they are consistent herewith. In one particularly suitable embodiment, the production animal is an avian animal such as a chicken, turkey, duck, or quail, and the antibody is isolated from the egg yolk of the egg of the avian animal.

In one embodiment, the egg yolk or serum including the antibodies are further dried to form a powder including the antibodies. The whole egg, egg yolk or parts of the egg may be spray dried. Serum may be separated from whole blood according to methods known by those skilled in the art. Spray drying of egg and serum may be performed using known spray drying methods and commercially available spray drying equipment. Dry egg and serum powders may also be prepared by lyophilization or vacuum drum drying. The dried egg, egg yolk or serum powder may then be introduced into animal feeds as a feed additive to transfer antibodies to an animal.

In another aspect, isolated antibodies can include antibodies in serum, or antibodies that have been purified to varying degrees. Such antibodies may include polyclonal antibodies, camelid antibodies, monoclonal antibodies, humanized or chimeric antibodies, anti-idiotypic antibodies, single chain antibodies, Fab fragments, fragments produced from a Fab expression library, epitope-binding fragments of the above, and the like. Production of antibodies is well-known in the art.

In yet another aspect, an antibody is isolated from the colostrum of an animal such as from bovine colostrum.

The methods disclosed herein can be achieved using food/feed additives including the IL-10 peptides, or isolated antibodies which specifically bind to IL-10 peptides.

As used herein, the term "feed" broadly refers to a material, liquid or solid, that is used for nourishing an animal, and for sustaining normal or accelerated growth of an animal including newborns or young and developing animals. The term includes a compound, preparation, mixture, or composition suitable for intake by an animal.

Specifically, the feed is suitable for herbivorous mammals such as cattle, horses, sheep and goats; for fish; or for companion animals. A feed composition comprises a basal food composition and one or more feed additives. The term "basal food composition" refers to a food composition combinable with additives such as the peptides and antibodies described herein. Basal animal food compositions may include components such as proteins, grains, flavor compositions, vitamins, minerals, preservatives, and the like. Basal food compositions can be suitable for ingestion by a target animal. The term "feed additive" as used herein refers to components included in small quantities for the purpose of fortifying basic feed with nutrients, stimulants, medicine, or to promote feed intake or alter metabolism. Feed additives include pre-mixes of biological compositions, or in the present disclosure, pre-mixes of IL-10 peptide or isolated antibody that specifically binds to IL-10 peptide.

In one embodiment, the methods disclosed herein are achieved using animal feed additive including IL-10 peptides including the amino acid sequence of any one of SEQ ID NOs. 1-34, and combinations thereof.

In another embodiment, the methods of the present disclosure utilize an animal feed additive including isolated antibodies that specifically bind to the IL-10 peptide including the amino acid sequence of SEQ ID NOs. 1-34, and combinations thereof.

The IL-10 peptides or isolated antibodies which specifically bind to IL-10 peptides may be added to an animal feed as a feed additive or mixed into an animal feed by a method known in the art for mixing feed additives and animal feed. In one embodiment, the IL-10 peptide or isolated antibody which specifically binds to the IL-10 peptide is directly added to the animal feed or mixed with the animal feed just prior to feeding the animal. In another embodiment, since feeds may be pelleted or extruded, the IL-10 peptide or isolated antibody which specifically binds to the IL-10 peptide may be coated on the surface of feed (pellet) after the feed has been pelleted or extruded (post pelleted application) in order to maintain functional properties of the IL-10 peptide or isolated antibody which specifically binds to the IL-10 peptide. The addition of the IL-10 peptide or isolated antibody which specifically binds to the IL-10 peptide post pelleting can be aided by mixing the IL-10 peptide or isolated antibody which specifically binds to the IL-10 peptide in water, oil, or another suitable carrier and spraying it on the pellets as they exit the pellet die.

The amount of the IL-10 peptide or isolated antibody that specifically binds to IL-10 peptide added and/or mixed with the animal feed depends on the feeding regimen and the type of feed for the animal, and may be determined by those skilled in the art. Typically, the amounts of IL-10 peptides and/or isolated antibodies to IL-10 peptide to be used in an animal feed are summarized in Table 2 below. Antibody prepared using other sources may be calculated as equivalents using Table 2.

TABLE 2

Dose of Anti-IL-10 Antibody in Animal Feed (mg/Kg diet) prepared using egg yolk antibody.

| Source | Low Dose | High Dose |
|---|---|---|
| Affinity purified anti-peptide | 0.0015 | 0.5 |
| Anti-peptide IgY | 0.015 | 50 |
| Dry Immune Yolk | 0.8 | 4000 |
| Dried Immune Whole Egg | 1.5 | 7500 |

The doses shown are based on the amount of epitope specific antibody in total IgY (1 to 10%), the amount of IgY in egg (5-10 mg/Kg of feed (dry matter)), antibody losses due to drying storage and gastrointestinal degradation.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

Specifically, the animal feed including the feed additive of either IL-10 peptide or isolated anti-IL-10 antibody is a feed for a non-human mammal such as a cow, horse, goat or sheep.

In one aspect, included herein is a milk composition suitable for administration to a pre-weaned mammal of a genus *Bos, Ovis, Capra, Bubalus* or *Sus* containing a basal milk composition and a therapeutically effective amount of an IL-10 peptide or anti-IL-10 antibody. Basal milk compositions include whole milk, waste milk, or a milk replacer composition. As used herein, a therapeutically effective amount of an IL-10 peptide or anti-IL-10 antibody is an amount effective to reduce the incidence of respiratory or gastrointestinal disease in the animal when administered daily for a period of 7 days to 7 weeks. Exemplary therapeutically effective amounts of interleukin-10 peptide or the isolated antibody that specifically binds an interleukin-10 peptide include 3 g/kg (dry matter) milk to 0.001 mg/Kg (dry matter) milk, specifically 1 g/Kg (dry matter) milk to 0.341 g/Kg (dry matter) milk. Exemplary peptides for inclusion in the milk compositions include the peptides of any one of SEQ ID Nos. 1-14, or combinations thereof. Exemplary anti-IL-10 antibodies for inclusion in milk compositions include antibodies that specifically bind a peptide of any one of SEQ ID NOs. 1-14, or any combination of antibodies.

In another aspect, included herein is a food composition suitable for administration to humans such as human children containing a basal food composition and an IL-10 peptide or anti-IL-10 antibody. A food composition suitable for administration to a human comprises a peptide of SEQ ID NO. 35, SEQ ID NO. 36, SEQ ID NO. 37, or SEQ ID NO. 38; or an isolated anti-IL-10 antibody that specifically binds a peptide of SEQ ID NO. 35, SEQ ID NO. 36, SEQ ID NO. 37, or SEQ ID NO. 38. Exemplary basal food compositions include milk, juice, formula, and solid foods such as snack food consumable by humans including human children.

In one embodiment, the methods involve injecting or orally administering an IL-10 peptide to an animal, thereby producing antibodies within the animal that specifically bind to the IL-10 peptide. IL-10 cytokine production is associated with down regulation of inflammation, and the IL-10 cytokine functions as an essential immunoregulator of the intestinal tract. The antibody to IL-10 peptide prevents the IL-10 cytokine from down regulating the immune system, thereby allowing the immune system to eliminate the pathogen.

In some embodiments, the methods involve injecting or orally administering an antibody to the IL-10 peptide to an animal. The term "animal", as used herein to describe animals administered an IL-10 peptide or isolated antibody to the IL-10 peptide in accordance with the present disclosure.

The invention is further illustrated by the following non-limiting examples.

EXAMPLES

Example 1: Anti-IL-10 Antibody Production

In this Example, the concentration of anti-IL-10 antibody production contained within the egg yolk of IL-10 peptide-administered producer hens was determined by using Enzyme-linked immunosorbent assay (ELISA) techniques.

Specifically, IL-10 peptide SEQ ID NO: 2 was conjugated to hen ovalbumin (OVA, Sigma, St. Louis, Mo.) for ELISA using a glutaraldehyde procedure. A 96-well Nunc™ immunosorbent F-series microplate (Sigma, St. Louis, Mo.) was coated with 100 μg/plate of peptide-specific OVA conjugate in sodium carbonate coating buffer having a pH of 9.6. The plate was allowed to coat overnight (100 μl/well) at 4° C. Dry egg yolk samples containing antibody to IL-10 Peptide SEQ ID NO. 2 were diluted 1:10 in acidic PBS having a pH of 4 and allowed to incubate overnight at 4° C. After overnight incubation, the antibody was extracted using centrifugation and used as a source of antibody to determine specificity for the peptide conjugated to the IL-10 peptide. The plate coated with OVA-peptide conjugate was washed 6 times with PBS/0.5% Tween solution, blocked with non-protein blocking buffer (200 μl/well, Pierce Scientific, Rockford, Ill.), and allowed to incubate at room temperature for at least 1 hour. The plate was washed 6 times and then samples of either adjuvant only injected control or egg antibody (isolated as described above) were added at a concentration of 100 μl/well in duplicate at 10× serial dilutions starting at 1:20. Primary antibodies were incubated for 1 hour, the plate was washed 6 times, and then secondary antibody (HRP-conjugated goat anti-chicken antibody, Bethyl Labs, Montgomery, Tex.) was diluted in blocking buffer 1:5000 and added at a concentration of 100 μl/well. Secondary antibody was incubated for 30 minutes, the plate was washed 6 times, and then substrate solution containing 19.74 ml 0.05M sodium acetate, 100 μl 20 mg/mL 3,3',5,5'

Tetramethyl Benzidine (TMB), 128 µl 0.5M H$_2$O$_2$ was added at a concentration of 125 µl/well and allowed to incubate until sufficient color development during the linear phase of development (blue color indicates primary antibody presence). A stop solution (0.5M sulfuric acid) was added to produce a yellow stable color and the plate was read at 450 nm on a Biotek EL800 plate reader. Triplicate optical densities were averaged and blocking buffer background was subtracted to produce a final optical density. The optical density of antibody to IL-10 peptide SEQ ID NO. 9 and FCA control were compared to determine specificity and dose level used in the final chick experiment (see Table 3).

TABLE 3

Antibody titer for cow anti-IL-10 antibody. Antibody extracts from control eggs and eggs from hens injected with an IL-10 peptide conjugate were serially diluted and added to plate bound peptide and analyzed as described above. The antibody to the IL-10 antibody could be diluted up to 1:320 (titer) before the absorbance equaled background absorbance.

| Dilution | Cow Anti-IL-10 | Control Antibody |
|---|---|---|
| 1:20 | 2.114 | 1.298333333 |
| 1:40 | 1.791 | 1.141333333 |
| 1:80 | 1.308 | 0.932666667 |
| 1:160 | 0.905666667 | 0.737333333 |
| 1:320 | 0.720666667 | 0.553666667 |
| 1:640 | 0.375 | 0.409666667 |
| 1:1280 | 0.254333333 | 0.294666667 |

Example 2: Field Trial to Evaluate the Effect of an Anti-IL-10 Antibody on *C. parvum* Oocyst Shedding and Other Health and Growth Parameters in Pre-Weaned Dairy Calves The study was a double-blinded, randomized, prospective clinical trial. There were 134 calves randomly assigned to a treatment group (72) and a control group (62) of primarily Holstein calves. Calves were enrolled in the study on five separate days within a 2-week period. On enrollment day, 23-28 calves (depending on the number of calves that arrived on the farm) were randomly assigned to a group designated by color (green=anti IL-10 IgY treatment, purple=anti IL-10 IgY treatment, orange=egg powder control group). Calf feeders, health screeners and investigators were blinded to the color code until the study was completed. Calves in this study originated from 12 surrounding dairy farms, where colostrum and newborn calf care were administered. Calves arrived between 1 and 3 days of age. On enrollment day, the data collected included body weight (electronic scale), hipometer (stall-side indirect measure of body weight), packed cell volume (PCV) and serum total protein concentration (indicator of dehydration and adequate passive transfer of immunoglobulins, respectively), and fecal pH. Calves were identified by group with color-coded zip ties on eartags and color-coded Duct Tape® on their individual hutches. The calves were fed in milk either 0.96 g of egg yolk powder containing anti IL-10 antibodies (treatment) or 0.96 g control egg yolk powder without anti-IL-10 antibodies (control egg yolk powder from hens receiving a sham inoculation) added to their milk daily (divided into 2 feedings) from Day 0 (day after enrollment) through Day 10. Attitude, appetite and health scores were recorded daily for 14 days using The Calf Health Scorer App. Fecal pH and fecal pathogen testing (*C. parvum* RT-PCR, Coronavirus RT-PCR, Rotavirus RT-PCR and *Salmonella* culture) were performed on Day 5 and Day 14 of the trial. Hydration status (PCV and serum total protein) and hipometer measurements were recorded on Day 7 and Day 14. Growth (average daily gain and hipometer) measurements along with health score were performed on Day 56 (for Calf Health Score) or when calves were moved out of the hutches. At this time, antibiotic administration data (by farm personnel) was also recorded.

The protocol deviations in the study were minor. The unequal group sizes are based on randomization using 3 colors assigned on the day that calves arrived. One calf died after enrollment and was removed from the study. Two missing data points on calf health scores and on enrollment fecal pH's, respectively were handled by leaving those calves out of the analysis of those specific data sets but not other parameters where the data collection was complete.

Experimental procedure: In this trial, 0.96 g egg yolk powder containing anti IL-10 IgY antibodies was added to the milk of calves in the treatment group while 0.96 egg yolk powder without anti IL-10 IgY antibodies was added to the milk of calves in the control group for 11 days. The dose of egg yolk powder administered in the milk was 1.2 gm/kg of milk dry matter, using an assumption of 12.5% dry matter for whole milk. The egg product used is defined by American Association of Feed Control Officials (AAFCO) 9.74.

Results: Average total health score and days of diarrhea were not significantly different between the two groups. There was a higher score for the diarrhea average score from Days 0 through Day 4 in the treated group (p=0.03). Rotavirus was significantly increased in the treatment group on Day 5 (p=0.02), but at Day 14 it was no longer significant. There was no significant difference in *C. parvum* oocyst shedding between the two groups. However, on Day 5 there was a trend (p=0.06) for increased *C. parvum* oocyst shedding in the treatment group, whereas the trend was reversed on Day 14 when there was decreased shedding of *C. parvum* oocysts in the treatment group. The mean cycle threshold value for *C. parvum* fecal PCR detection was higher in the treatment group than the control group on Day 14, another indicator of reduced *C. parvum* oocyst shedding in anti IL-10 antibody treated calves. Fecal pH was significantly higher in the treatment group at Day 14 (p=0.004). The differences in fecal pH from enrollment day to Day 5, enrollment day to Day 14 and Day 5 to Day 14 were all significantly higher in the treatment group. A more alkaline fecal pH is associated with improved digestion and overall gastrointestinal health.

TABLE 4

Fecal pH of control or anti-IL-10 antibody treated calves and the change from start date (E) to day 5 and 14, or from day 5 to 14.

| | Control | Treatment |
|---|---|---|
| Day E | 5.95$^a$ | 5.78$^b$ |
| Day 5 | 5.32$^a$ | 5.38$^a$ |
| Day 14 | 6.35$^a$ | 6.67$^b$ |
| Day 5-E | −0.64$^a$ | −0.40$^b$ |
| Day 14-E | 0.39$^a$ | 0.89$^b$ |
| Day 14-5 | 1.03$^a$ | 1.30$^b$ |

Average daily gain was significantly increased in the control group (p=0.04) but the hipometer measurement from Day 0 to Day 56 was significantly higher in the treated group (p=0.02). The latter finding is indicative of a larger frame size (width between the greater trochanter of the left and right femurs) in treated calves, even though average daily gain was greater in the control calves.

The prevalence of respiratory disease on Day 56, as determined by the calculated total respiratory score, was significantly higher in the control group (21%) versus the treated group (8%) (p=0.04). In addition, use of antibiotics by farm personnel for respiratory disease (investigators excluded antibiotic treatment for joint or navel infections) was significantly higher in the control group (20.7%) versus the treated group (7.2%) (p=0.04).

General discussion and conclusions: Dairy calf health is significantly affected by both enteric disease (most severely in the preweaning period) and by pneumonia (most commonly in the postweaning period). Antibiotic therapy is commonly used to treat both enteric and respiratory pathogens, leading to issues regarding antibiotic resistance, withdrawal times and residues. *Cryptosporidium parvum* is an Apicomplexan protozoan that infects intestinal cells and destroys villi, causing a malabsorptive diarrhea. The shedding prevalence of *C. parvum* is reported in the United States as 8 to 49% in calves and 6 to 13% in adult cows. Within-farm prevalence can be high as 70% on some farms, and both shedding and intensity of shedding have been significantly associated with diarrhea. *C. parvum* and Rotavirus have been found to be the most common enteric pathogens in diarrheic feces and most calves with diarrhea have more than one pathogen isolated from their feces. Oral IgY products have been successful in treating gastrointestinal infections, including bovine rotavirus, coronavirus, enterotoxigenic *E. coli*, and *Salmonella* spp. Although orally administered IgY is proteolytically digested to Fab and Fc fragments, both show neutralizing activity in the GI tract and can be detected in feces. Previous studies have shown that IL-10 expression is increased in calves infected with *C. parvum*. In addition, IL-10 knockout mice have been found to be significantly resistant to *C. parvum* infection. The present study was conducted to investigate the effects of feeding anti-IL-10 egg yolk antibodies on fecal pathogen shedding, health, and weight gain in dairy calves. The results showed a trend in reduced *C. parvum* shedding when evaluating the cycle threshold values at day 14 (p=0.08) and a significant increase in fecal pH in the treatment group. Fecal pH is an indicator of colonic acidity, as nutrients that escape digestion in the small intestine ferment in the large bowel. It has been shown that decreased fecal pH in dairy calves is associated with elevated lactate production and reduced volatile fatty acid concentrations in the colon (VFAs). Absorption of VFAs from the large intestine is critical for promoting sodium and water reabsorption in the gut. Without being held to theory, we associate the significant increase in fecal pH and the trend towards reducing fecal shedding of *C. parvum* in the treatment group as indicators of improved gastrointestinal health. The increased shedding of rotavirus could be related to increased passthrough of the virus without attachment to the small intestinal villi.

An unanticipated benefit to the treatment group was a decrease in respiratory disease and less antibiotic usage than the control group during the trial (day 0-day 56) (FIG. 1). Without being held to theory, it is proposed that the mechanism relating gastrointestinal health with respiratory disease resistance is due to cross-talk between the respiratory and gastrointestinal mucosal surfaces. Mucosa-associated lymphoid tissue (MALT) directs antigen processing, lymphoid cell trafficking, and local host defenses. This resident lymphoid tissue within the respiratory and gastrointestinal tracts has a common embryonic origin in the primitive foregut. Thus, feeding anti IL-10 IgY antibodies to neonatal calves may have far-reaching effects on overall calf health, welfare, performance and profitability. Any ability to reduce antibiotic use in neonatal dairy calves can promote a more balanced gastrointestinal microbiome, improve the susceptibility of pathogens when antibiotics are needed, and reduce antibiotic resistance, a major goal of the food animal industry.

In summary, the results presented herein suggest that improved gastrointestinal health is linked to improved respiratory immunity utilizing the common mucosal immune system hypothesis. From this study, there is evidence of improved gastrointestinal tract health in enteric pH data; there is a trend for reduced *C. parvum* oocyst shedding, and improved frame size in neonatal calves given anti IL-10 antibody for 11 days. With improved digestive function, there appear to be combined benefits of improved enteric and respiratory mucosal immunity. The significant reduction in respiratory disease in dairy calves at weaning has the potential to decrease respiratory disease in post weaning group housing. Respiratory disease in this age group has significant negative long term economic and welfare consequences of recurring disease, poor growth, delayed breeding, reduced milk production in the first lactation and early culling.

Example 3: Second Field Trial

The proposed second field trial will investigate a dose response to anti IL-10 antibody feeding (0, 0.5, 1 and 2 times the dose used in trial 1 and a farm control group) and will prolong inclusion in the diet for 14 days, when the risk of neonatal diarrhea is greatly reduced. Parameters of health monitoring, gastrointestinal function, fecal pathogen shedding, growth and antibiotic usage will be similar to trial 1 but, to validate the finding of reduced respiratory disease prevalence in trial 1, health and respiratory disease parameters will be monitored twice weekly for the entire 56-day clinical trial. Thoracic ultrasound and respiratory pathogen detection by deep nasopharyngeal swab sampling will confirm that respiratory disease is present and help define the benefit of feeding anti IL-10 antibody.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of reducing a symptom of a bovine respiratory disease complex in a pre-weaned bovine, comprising orally administering to the pre-weaned bovine an effective amount of an egg yolk preparation comprising an isolated antibody that specifically binds an interleukin-10 peptide of SEQ ID NO:2, wherein said antibody is a polyclonal avian egg yolk IgY antibody preparation produced by inoculating laying hens with the interleukin-10 peptide of SEQ ID NO:2; wherein administration is initiated between birth and weaning, and wherein administration is performed at least once daily for a period of 7 days to 7 weeks; and wherein the symptom of bovine respiratory disease complex is increased fecal *Cryptosporidium parvum*, reduced weight gain, decreased fecal pH, or a combination thereof.

2. The method of claim 1, wherein administration of the egg yolk preparation is stopped after the 7 day to 7 week period and is not restarted for 1 to 14 days.

3. The method of claim 1, wherein the bovine is 56 days of age or younger.

4. The method of claim 1, wherein the egg yolk preparation comprising the isolated antibody that specifically binds the interleukin-10 peptide is administered in a milk composition.

* * * * *